US00PP35094P2

(12) United States Plant Patent
Trees

(10) Patent No.: US PP35,094 P2
(45) Date of Patent: Apr. 11, 2023

(54) ***LANTANA* PLANT NAMED 'SAILAN004'**

(50) Latin Name: *Lantana camara*
Varietal Denomination: SAILAN004

(71) Applicant: Sakata Seed America, Inc., Morgan Hill, CA (US)

(72) Inventor: Scott C. Trees, Arroyo Grande, CA (US)

(73) Assignee: SAKATA SEED AMERICA, INC., Morgan Hill, CA (US)

( * ) Notice: Subject to any disclaimer, the term of this patent is extended or adjusted under 35 U.S.C. 154(b) by 28 days.

(21) Appl. No.: 17/898,696

(22) Filed: Aug. 30, 2022

(51) Int. Cl.
*A01H 5/02* (2018.01)
*A01H 6/86* (2018.01)

(52) U.S. Cl.
USPC ..... Plt./227

(58) Field of Classification Search
USPC ..... Plt./226, 227
See application file for complete search history.

*Primary Examiner* — Karen M Redden
(74) *Attorney, Agent, or Firm* — Weatherly IP Solutions, LLC; Jamses M. Weatherly

(57) ABSTRACT

A new *Lantana* plant designated 'SAILAN004' particularly distinguished by a vigorous, semi-mounding growth habit, with inflorescences having colors of yellow, pink and combinations of pink and yellow, is disclosed.

3 Drawing Sheets

Genus and species: *Lantana camara.*
Variety denomination: 'SAILAN004'.

BACKGROUND

The present invention relates to a new and distinct cultivar of *Lantana* plant botanically known as *Lantana camara* and hereinafter referred to by the cultivar name 'SAILAN004'.

The new cultivar originated in a controlled breeding program in Guadalupe, Calif. during June 2015. The objective of the breeding program was the development of *Lantana* cultivars having pink flowers and a vigorous, semi-mounding habit.

The new *Lantana* cultivar is the result of cross-pollination. The female (seed) parent of the new cultivar is the proprietary *Lantana camara* breeding selection coded 18233, not patented, characterized by its medium rose-pink colored inflorescences, medium green colored foliage, and vigorous, mounded growth habit. The male (pollen) parent of the new cultivar is the proprietary *Lantana camara* breeding selection coded 9063, not patented, characterized by its medium pink-colored inflorescences, medium green colored foliage, low growth vigor and compact-mounded growth habit. The new cultivar was selected as a single flowering plant within the progeny of the above stated cross-pollination during May 2016 in a controlled environment in Guadalupe, Calif.

Asexual reproduction of the new cultivar by terminal stem cuttings since May 2016 in Guadalupe, Calif. and Salinas, Calif. has demonstrated that the new cultivar reproduces true to type with all of the characteristics, as herein described, firmly fixed and retained through successive generations of such asexual propagation.

SUMMARY

The following characteristics of the new cultivar have been repeatedly observed and can be used to distinguish 'SAILAN004' as a new and distinct cultivar of *Lantana* plant:

1. Vigorous, semi-mounding growth habit; and
2. Inflorescences with yellow, pink, and yellow-pink color combinations.

BRIEF DESCRIPTION OF THE PHOTOGRAPHS

The accompanying photographs were taken on Sep. 2, 2021 and show, as nearly true as it is reasonably possible to make the same in color illustrations of this type, typical flower and foliage characteristics of the new cultivar. Colors in the photographs may differ slightly from the color values cited in the detailed description, which accurately describes the colors of 'SAILAN004'.

DETAILED BOTANICAL DESCRIPTION

Figure 1:
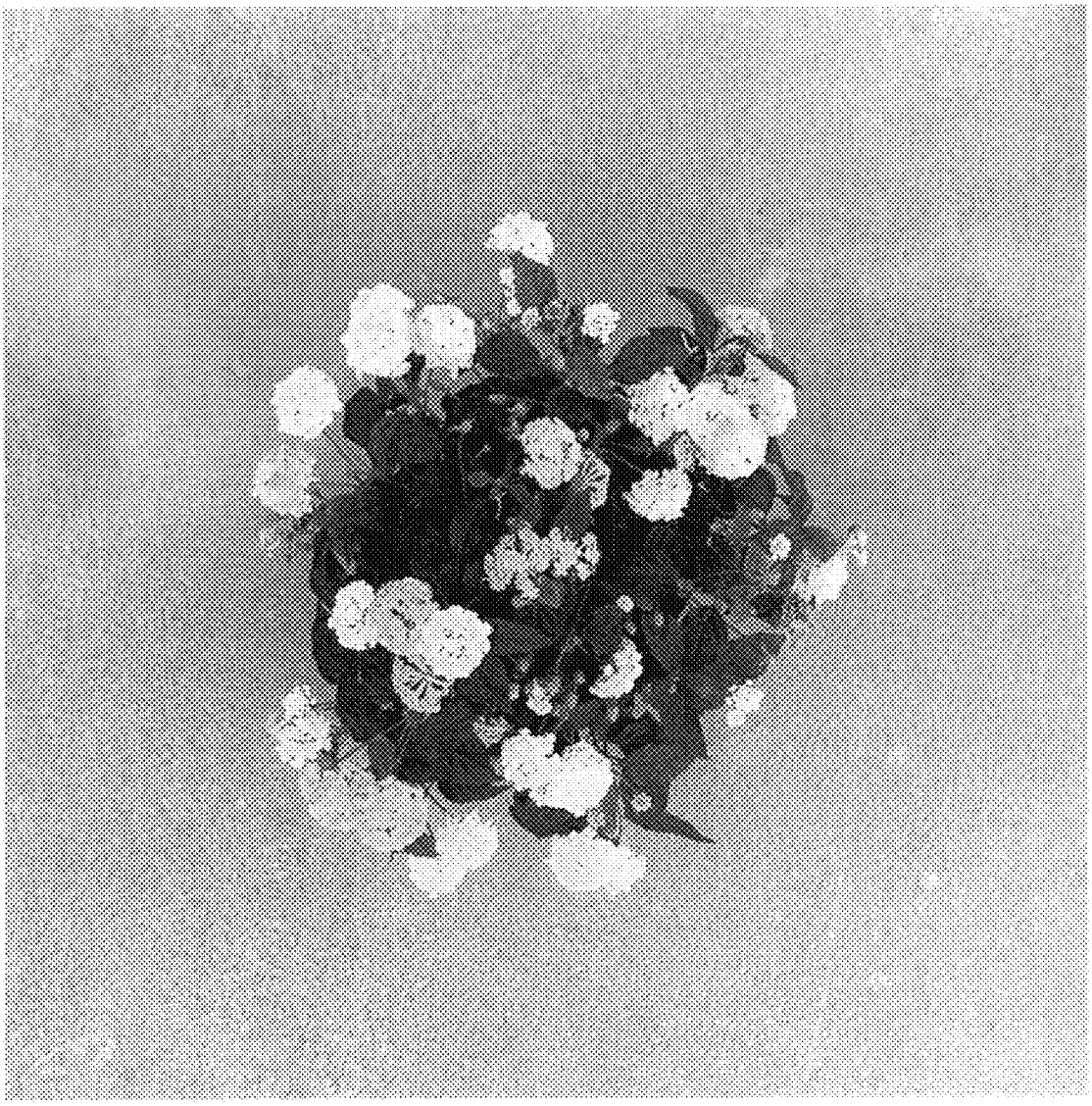
FIG. 1 illustrates a top view of the overall growth and flowering habit of 'SAILAN004'.
Figure 2:
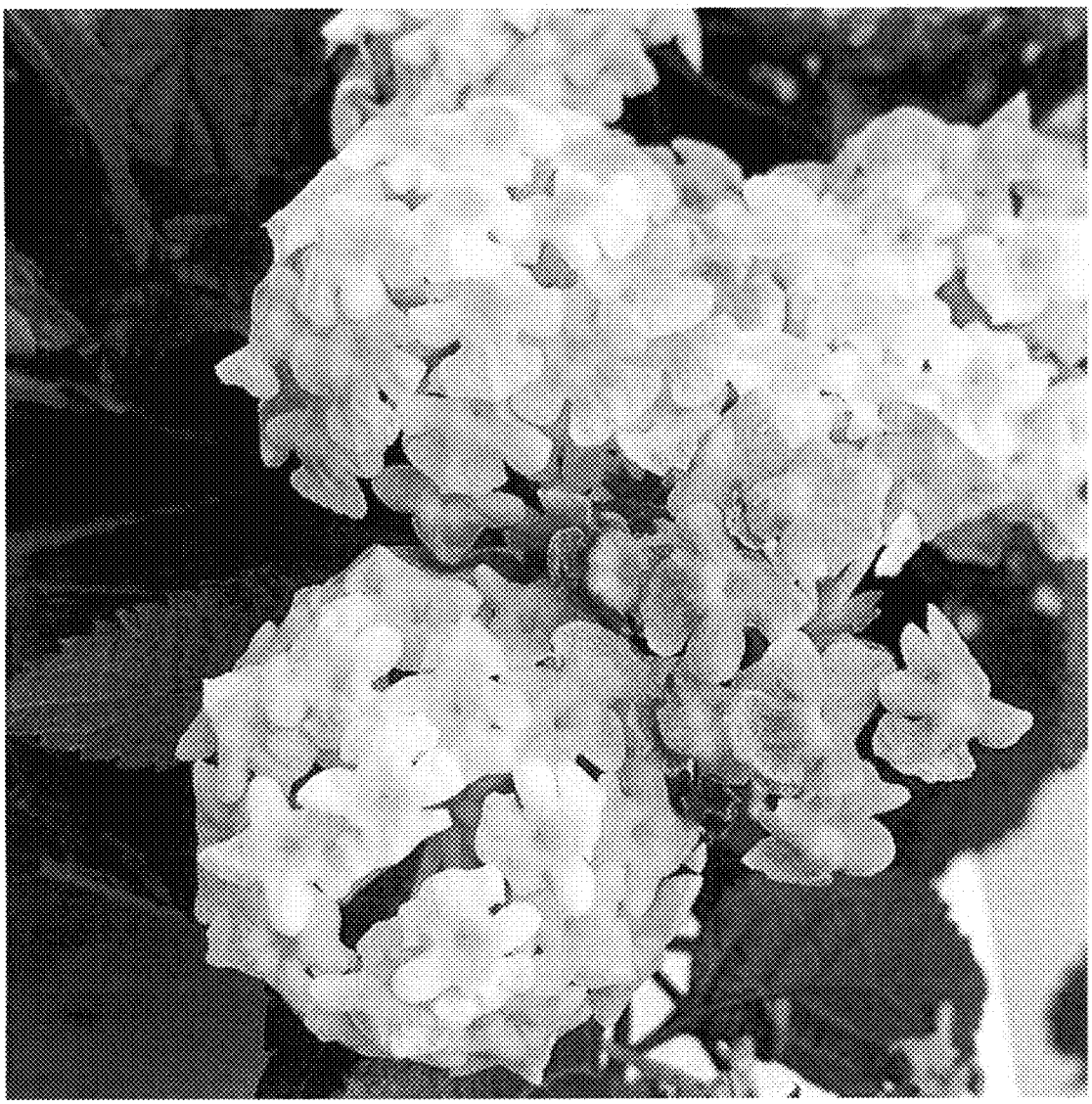
FIG. 2 illustrates a close-up view of an individual inflorescence of 'SAILAN004'.
Figure 3:
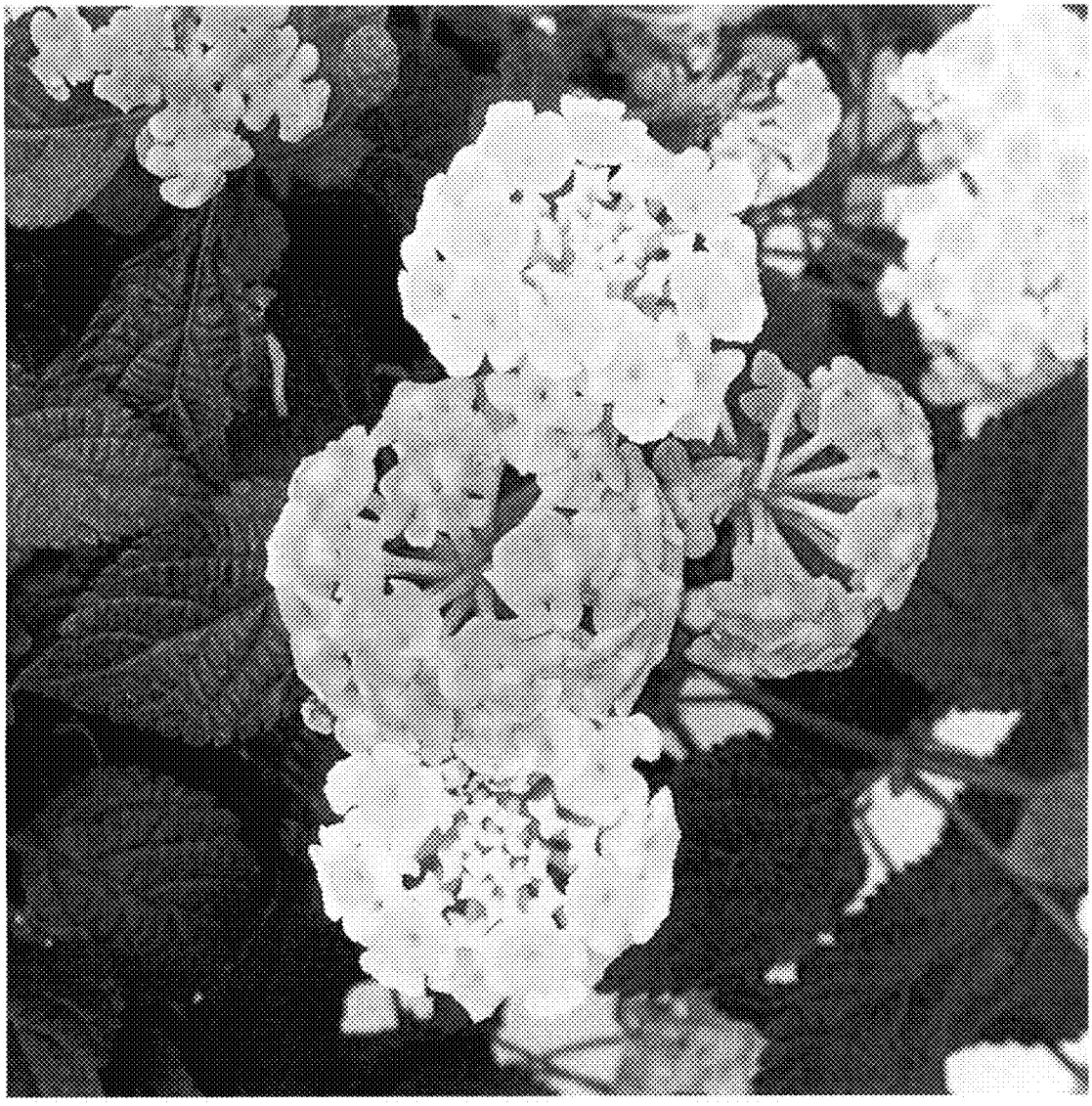
FIG. 3 illustrates a close-up view of an individual inflorescence of 'SAILAN004'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used.

The following descriptions and measurements were collected in September of 2021 and obtained from plants grown 2 months from transplant into gallon pots from rooted cuttings in Salinas, Calif., under greenhouse conditions.

Botanical classification:

*Genus and species.*—*Lantana camara.*

*Variety.*—'SAILAN004'.

*Parentage.*—Female parent: '18233', not patented. Male parent: '9063', not patented.

Growth:

*Type cutting.*—Terminal stem.

*Time to initiate roots.*—Approximately 7 to 11 days.

*Time to produce a rooted cutting.*—Approximately 35 to 42 days.

*Root description.*—Fibrous; woody.

*Rooting habit.*—Freely branching. The terminal 1.0 to 1.5 inches of an actively growing stem was excised. The vegetative cuttings were propagated in five to six weeks. The base of the cuttings were dipped for 1 to 2 seconds in a 1:9 solution of Dip'N Grow (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24C.

Plant description:

*Commercial crop time.*—Approximately 6 to 7 weeks from a rooted cutting to finish in a 10 cm pot.

*Growth habit and general appearance.*—Moderately vigorous, semi-mounding.

*Height from soil level to top of plant plane.*—Approximately 17.0 cm.

*Width.*—Approximately 41.0 cm.

*Branching habit.*—Freely branching, pinching enhances branching.

*Quantity of lateral branches per plant.*—1 main that splits off into 4 smaller and 1 lateral.

Branch:

*Shape.*—Square in cross section.

*Strength.*—Strong, becomes woody with age.

*Length.*—Approximately 12.0 cm to 19.0 cm to end of inflorescences.

*Diameter.*—Approximately 4.0 mm.

*Length of central internode.*—Approximately 3.5 cm.

*Texture.*—Pubescent, short rough pubescence.

*Gland color.*—Not observed.

*Color of young stem.*—RHS 144A (Strong Yellow Green).

*Color of mature stem.*—Closest to RHS 199C (Light Yellowish Brown).

Foliage description:

*Quantity of leaves per lateral branch.*—Approximately 30 to 40.

*Fragrance.*—Peppery.

*Form.*—Simple.

*Arrangement.*—Opposite.

*Aspect.*—Right or acute angle to stem.

*Shape.*—Ovate.

*Margin.*—Serrate.

*Apex.*—Acuminate.

*Base.*—Decurrent.

*Venation pattern.*—Entire.

*Length of mature leaf.*—Approximately 5.5 cm.

*Width of mature leaf.*—Approximately 2.7 cm.

*Texture of upper surface.*—Scabrous; rough.

*Texture of lower surface.*—Scabrous and glandular pubescent along venation.

*Gland color.*—Not observed.

*Vein color upper.*—RHS 147B (Moderate Yellow Green).

*Vein color lower.*—RHS 147C (Moderate Yellow Green).

*Color of upper surface.*—Closest to but much darker than RHS NN137A (Greyish Olive Green).

*Color of lower surface.*—Closest to but much darker than RHS 191A (Greyish Yellow Green).

Petiole:

*Length.*—Approximately 11.0 mm.

*Diameter.*—Approximately 1.5 mm.

*Texture.*—Lightly pubescent with a RHS NN155D color (White).

*Gland color.*—Not Observed.

*Color.*—RHS 146B (Moderate Yellow Green).

Flowering description:

*Flowering habit.*—'SAILAN004' is freely flowering under outdoor growing conditions with substantially continuous blooming from spring through autumn and year-round in greenhouse environment.

*Lastingness of individual inflorescence on the plant.*—Approximately 7 to 10 days from first color of outer buds to dropping of last flower.

Inflorescence description:

*Type.*—Umbel.

*Quantity per plant.*—Approximately 30.

*Fragrance.*—Strong, spicy.

*Aspect.*—Facing upward or outward.

*Height.*—Approximately 2.0 cm.

*Width.*—Approximately 3.5 cm.

*Quantity of fully open flowers per inflorescence.*—Approximately 31.

Peduncle:

*Strength.*—Strong; flexible.

*Shape.*—Square in cross section.

*Aspect.*—Acute angle to stem.

*Length.*—Approximately 4.0 cm.

*Diameter.*—Approximately 1.0 mm to 2.0 mm.

*Texture.*—Lightly scabrous.

*Color.*—RHS 143B (Strong Yellow Green).

Flower description:

*Type.*—Salverform.

Bud:

*Rate of opening.*—Generally takes 1 to 2 days for bud to progress from first color to fully open flower. Buds open in progression from the margin to the center of the inflorescence.

*Quantity of unopened inflorescences per plant.*—Approximately 12.

*Shape.*—Elongated, rectangular at apex.

*Length.*—Approximately 10.0 cm.

*Diameter.*—Approximately 3.0 mm.

*Color.*—RHS 2D (Pale Greenish Yellow).

Corolla:

*Depth*.—Approximately 1.3 cm.

*Diameter*.—Approximately 11.0 mm.

Petals:

*Quantity*.—4.

*Description*.—Non-imbricate, non-symmetrical petals. Petals are fused at base forming a corolla tube.

*Shape*.—Obovate.

*Appearance*.—Dull.

*Aspect*.—Cupped.

*Margin*.—Entire, slightly ruffled.

*Apex*.—Obtuse.

*Length of upper petal from throat*.—Approximately 4.0 mm.

*Width of upper petal*.—Approximately 8.0 mm.

*Length of lateral petals from throat*.—Approximately 4.5 mm.

*Width of lateral petals*.—Approximately 4.5 mm.

*Length of lower petal from throat*.—Approximately 7.0 mm.

*Width of lower petal*.—Approximately 7.0 mm.

*Texture of upper and lower surface*.—Glabrous.

*Gland color*.—Not Observed.

*Color of upper surface*.—Has yellow, pink, and a yellow-pink combination, turning completely pink at maturity. Yellow: RHS 155B (Yellowish White) with eye of RHS 6A (Bright Greenish Yellow). Pink: RHS 76C (Very Pale Purple) with RHS 70B (Strong Reddish Purple) toward center.

*Color of lower surface*.—Yellow: 11D (Pale Yellow). Pink: Closest to 67D (Very Pale Purple).

Corolla tube:

*Length*.—Approximately 1.2 cm.

*Diameter at midpoint*.—Approximately 2.0 mm.

*Texture of inner and outer surface*.—Glabrous.

*Pubescence color*.—None.

*Color of inner surface*.—Yellow flowers: RHS 4B (Light Greenish Yellow). Pink flowers: RHS 155B (Yellowish White).

*Color of outer surface*.—Yellow flowers: RHS 1C (Light Greenish Yellow). Pink flowers: RHS 155C (Greenish White).

Calyx:

*Shape*.—Tubular with two broadly acute tips.

*Length*.—Approximately 2.0 mm.

*Diameter*.—Approximately 2.0 mm.

*Texture of inner and outer surface*.—Glabrous.

*Gland color*.—Not Observed

*Color of inner and outer surfaces*.—145B (Light Yellow Green).

Bracts:

*Quantity per flower*.—1 per flower.

*Shape*.—Linguate.

*Length*.—Approximately 6.0 mm.

*Width*.—Approximately 1.5 mm.

*Texture of upper and lowers surface*.—Slightly pubescent. RHS NN155D (White).

*Color of upper and lower surfaces*.—Closest to but darker than RHS 143A (Strong Yellow Green) at apex lightening to RHS 144C (Light Yellow Green) at base.

Reproductive organs:

*Androecium*.—Stamen quantity: 4 per flower, adnate to corolla tube. Stamen length: Approximately 1.0 mm. Anther shape: Bilobed, ovoid. Anther length: Approximately less than 1.0 mm. Anther color: RHS 163B (Strong Orange Yellow). Pollen amount: Moderate. Pollen Color: RHS 162B (Moderate Yellow).

*Gynoecium*.—Pistil quantity: 1 per flower. Pistil length: Approximately 3.0 mm. Stigma shape: Funnel. Stigma length: Less than 1.0 mm. Stigma color: RHS 144A (Strong Yellow Green). Style length: Approximately 2.9 mm. Style color: RHS 160D (Pale Yellow). Ovary diameter: Approximately 1.0 mm. Ovary color: RHS 144A (Strong Yellow Green).

Seed and fruit production: Neither seed nor fruit production has been observed.

Disease and pest resistance: Resistance to pathogens and pests common to *Lantana* has not been observed.

COMPARISON OF 'SAILAN004' WITH PARENTAL LINES AND KNOWN VARIETY

'SAILAN004' is distinguished from the parental lines as described in Table 1.

TABLE 1

Comparison with Parental Lines

| Trait | Variety 'SAILAN004' | Female parent '18233' | Male parent '9063' |
|---|---|---|---|
| Inflorescense color | RHS 76C (Very Pale Purple) with RHS 70B (Strong Reddish Purple) toward center. | Rose Pink; darker than SAILAN004. | Medium Pink; Darker than SAILAN004. |
| Growth habit | Vigorous, semi-mounding. | More vigrous than SAILAN004. | Less vigorous than SAILAN004. |

Plants of the new cultivar differ from plants of the female parent primarily in having inflorescences that include lighter pink-colored florets and less growth vigor. Plants of the new cultivar differ from plants of the male parent primarily in having inflorescences that include lighter pink-colored florets and increased growth vigor.

'SAILAN004' can be compared to the commercial *Lantana* variety 'Baloomink' (U.S. Plant Pat. No. 33,389). Differences between the varieties are described in Table 2.

TABLE 2

Comparison with Similar Variety

| | 'SAILAN004' | 'Baloomink' |
|---|---|---|
| Corolla Tube Outer Color | RHS 155C (Greenish White) | RHS 145D with an overlay of RHS NN74B, overlay becomes heavier with age. |
| Petal Upper Surface Color | RHS 76C (Very Pale Purple) with RHS 70B (Strong Reddish Purple) toward center. | RHS 12A with distal half of RHS 12D, transitions with age to RHS 12D with and overlay of RHS NN74D. |

I claim:

1. A new and distinct variety of *Lantana* plant designated 'SAILAN004' as illustrated and described herein.

* * * * *